United States Patent
Hamada et al.

(10) Patent No.: US 10,849,515 B2
(45) Date of Patent: Dec. 1, 2020

(54) IMAGE PROCESSING APPARATUS AND PULSE ESTIMATION SYSTEM PROVIDED THEREWITH, AND IMAGE PROCESSING METHOD

(71) Applicant: PANASONIC INTELLECTUAL PROPERTY MANAGEMENT CO., LTD., Osaka (JP)

(72) Inventors: Masao Hamada, Fukuoka (JP); Tadanori Tezuka, Fukuoka (JP); Tsuyoshi Nakamura, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 272 days.

(21) Appl. No.: 15/769,961

(22) PCT Filed: Sep. 2, 2016

(86) PCT No.: PCT/JP2016/004014
§ 371 (c)(1),
(2) Date: Apr. 20, 2018

(87) PCT Pub. No.: WO2017/072998
PCT Pub. Date: May 4, 2017

(65) Prior Publication Data
US 2018/0310845 A1 Nov. 1, 2018

(30) Foreign Application Priority Data
Oct. 29, 2015 (JP) .................................. 2015-213348

(51) Int. Cl.
*G06K 9/00* (2006.01)
*A61B 5/024* (2006.01)
(Continued)

(52) U.S. Cl.
CPC ........ *A61B 5/02427* (2013.01); *A61B 5/0245* (2013.01); *A61B 5/7203* (2013.01);
(Continued)

(58) Field of Classification Search
None
See application file for complete search history.

(56) References Cited

U.S. PATENT DOCUMENTS

| 2013/0083847 | A1* | 4/2013 | Takeda | H04N 19/61 |
| | | | | 375/240.12 |
| 2017/0112382 | A1* | 4/2017 | Nakata | A61B 5/00 |
| 2017/0328726 | A1* | 11/2017 | Matsuzawa | G01C 21/26 |

FOREIGN PATENT DOCUMENTS

| JP | 2005-130362 | 5/2005 |
| JP | 2012-239661 | 12/2012 |
| JP | 2014-200390 A | 10/2014 |

OTHER PUBLICATIONS

The Extended European Search Report dated Jul. 16, 2018 for European Patent Application No. 16859239.2.
(Continued)

*Primary Examiner* — Wei Wen Yang
(74) *Attorney, Agent, or Firm* — Greenblum & Bernstein, P.L.C.

(57) ABSTRACT

Image processing apparatus is provided with data compression processing unit that executes data compression processing on an input captured image based on inter-frame prediction; and operation-mode selection unit that is capable of selecting one of a first operation mode for normal imaging and a second operation mode for pulse estimation based on a command from a user. In a case where the second operation mode is selected, data compression processing unit sets an interval between I pictures constituting a compressed image generated by the data compression processing
(Continued)

to an interval to be different from that in a case where the first operation mode is selected.

8 Claims, 8 Drawing Sheets

(51) Int. Cl.
| | |
|---|---|
| *H04N 19/107* | (2014.01) |
| *H04N 19/117* | (2014.01) |
| *H04N 19/114* | (2014.01) |
| *H04N 19/162* | (2014.01) |
| *A61B 5/0245* | (2006.01) |
| *H04N 19/179* | (2014.01) |
| *H04N 19/157* | (2014.01) |
| *H04N 19/86* | (2014.01) |
| *H04N 19/159* | (2014.01) |
| *H04N 19/46* | (2014.01) |
| *A61B 5/00* | (2006.01) |

(52) U.S. Cl.
CPC ......... *A61B 5/7232* (2013.01); *H04N 19/107* (2014.11); *H04N 19/114* (2014.11); *H04N 19/117* (2014.11); *H04N 19/157* (2014.11); *H04N 19/159* (2014.11); *H04N 19/162* (2014.11); *H04N 19/179* (2014.11); *H04N 19/46* (2014.11); *H04N 19/86* (2014.11); *A61B 2576/00* (2013.01)

(56) References Cited

OTHER PUBLICATIONS

McDuff Daniel J et al: "A Survey of Remote Optical Photoplethysmographic Imaging Methods", 2015 37th Annual International Conference of the IEEE Engineering in Medicine and Biology Society (EMBC), IEEE, Aug. 25, 2015 (Aug. 25, 2015), pp. 6398-6404, XP032811664.

Qian Daxing et al: "A Novel Method of Adaptive GOP Structure Base on Coding Efficiency and Complexity Joint Model", Fifth International Conference on Intelligent Control and Information Processing, IEEE, Aug. 18, 2014 (Aug. 18, 2014), pp. 239-243, XP032720150.

Sungjun Kwon et al: "Validation of heart rate extraction using video imaging on a built-in camera system of a smartphone", Engineering in Medicine and Biology Society (EMBC), 2013 35th Annual International Conference of the IEEE, IEEE, Aug. 28, 2012 (Aug. 28, 2012), pp. 2174-2177, XP032463369.

Official Communication issued in International Pat. Appl. No. PCT/JP2016/004014, dated Nov. 22, 2016.

\* cited by examiner

IMAGE PROCESSING APPARATUS AND PULSE ESTIMATION SYSTEM PROVIDED THEREWITH, AND IMAGE PROCESSING METHOD

TECHNICAL FIELD

The present disclosure relates to a technique for estimating a pulse from a human image without being in contact with a human body, and in particular, to an image processing apparatus for acquiring an image suitable for estimating a pulse, a pulse estimation system provided therewith, and an image processing method.

BACKGROUND ART

Regarding measurement of a pulse of a person, there are a method in which a measuring person (nurse or the like) puts his/her finger on a wrist of a subject to personally check pulsation, a method in which a dedicated measuring instrument is attached to a wrist, a finger, or the like of a subject to automatically detect pulsation, and the like. On the other hand, in such a measuring method, since free movement of the subject is temporarily restricted or it is necessary to attach the measuring instrument to the subject, a technique for estimating (detecting) a pulse without being in contact with the subject (human body) has been developed.

For example, regarding to a technique for detecting a heart rate (usually equivalent to a pulse rate) without being in contact with the human body, a heart rate detection apparatus, in which a spectral distribution of a time-series signal is extracted from image data obtaining by capturing a subject, and a peak frequency caused by a heartbeat signal is specified from the spectral distribution to automatically detect the heart rate, is known (see PTL 1).

However, with respect to an image (moving image) captured by a camera, since a data amount tends to be large, a data compression technique (for example, Moving Picture Experts Group (MPEG) standard data encoding method) for facilitating storage, transmission, and reception of image data has become widespread.

However, in a case where a pulse is estimated from a face image captured by the camera, a variation amount (that is, a variation amount of a pixel value) of a pulse signal extracted from the image data is very small. Therefore, regarding the image to which the data compression as described above is applied, there are cases where it is difficult to estimate the pulse or the accuracy of the estimation is remarkably deteriorated. More specifically, for example, regarding an image to which data compression processing is applied by using inter-frame prediction, in a case where the pulse is estimated by frequency analysis, when an Intra Picture (I picture) is switched to a Predictive Picture (P picture), or the P picture is switched to the I picture in a group of picture (GOP), a frequency component (noise) close to a frequency component of the pulse may occur in the spectral distribution described above.

A primary object of the present disclosure is to appropriately execute data compression processing of an image, thereby making it possible to acquire an image suitable for estimation of a pulse while suppressing an increase in a data amount of the image.

CITATION LIST

Patent Literature

PTL 1; Japanese Patent Unexamined Publication No. 2012-239661

SUMMARY OF THE INVENTION

An image processing apparatus of the present disclosure that acquires an image for estimating a pulse includes a data compression processing unit that executes data compression processing on an input captured image based on inter-frame prediction; and an operation-mode selection unit that is capable of selecting one of a first operation mode for normal imaging and a second operation mode for pulse estimation based on a command of a user. In a case where the second operation mode is selected, the data compression processing unit sets an interval between I pictures constituting a compressed image generated by the data compression processing to an interval to be different from that in a case where the first operation mode is selected.

According to the present disclosure, the data compression processing of the image is appropriately executed, and thereby it is possible to acquire an image suitable for the estimation of the pulse while suppressing an increase in a data amount of the image.

DESCRIPTION OF EMBODIMENTS

Hereinafter, embodiments of the present disclosure will be described with reference to the drawings.

Figure 1:
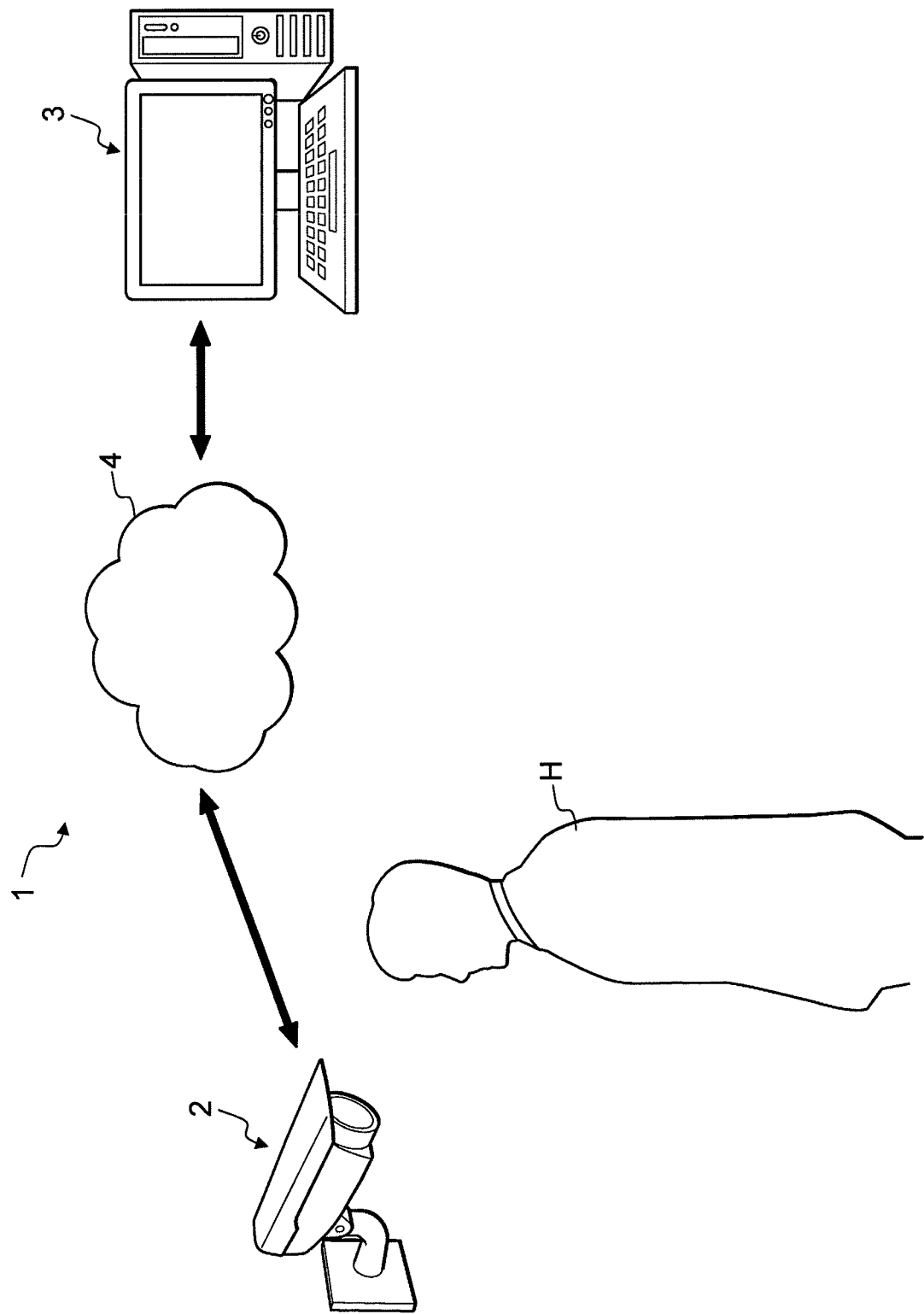
FIG. 1 is a view of an entire configuration of a pulse estimation system according to the present disclosure.
Figure 2:
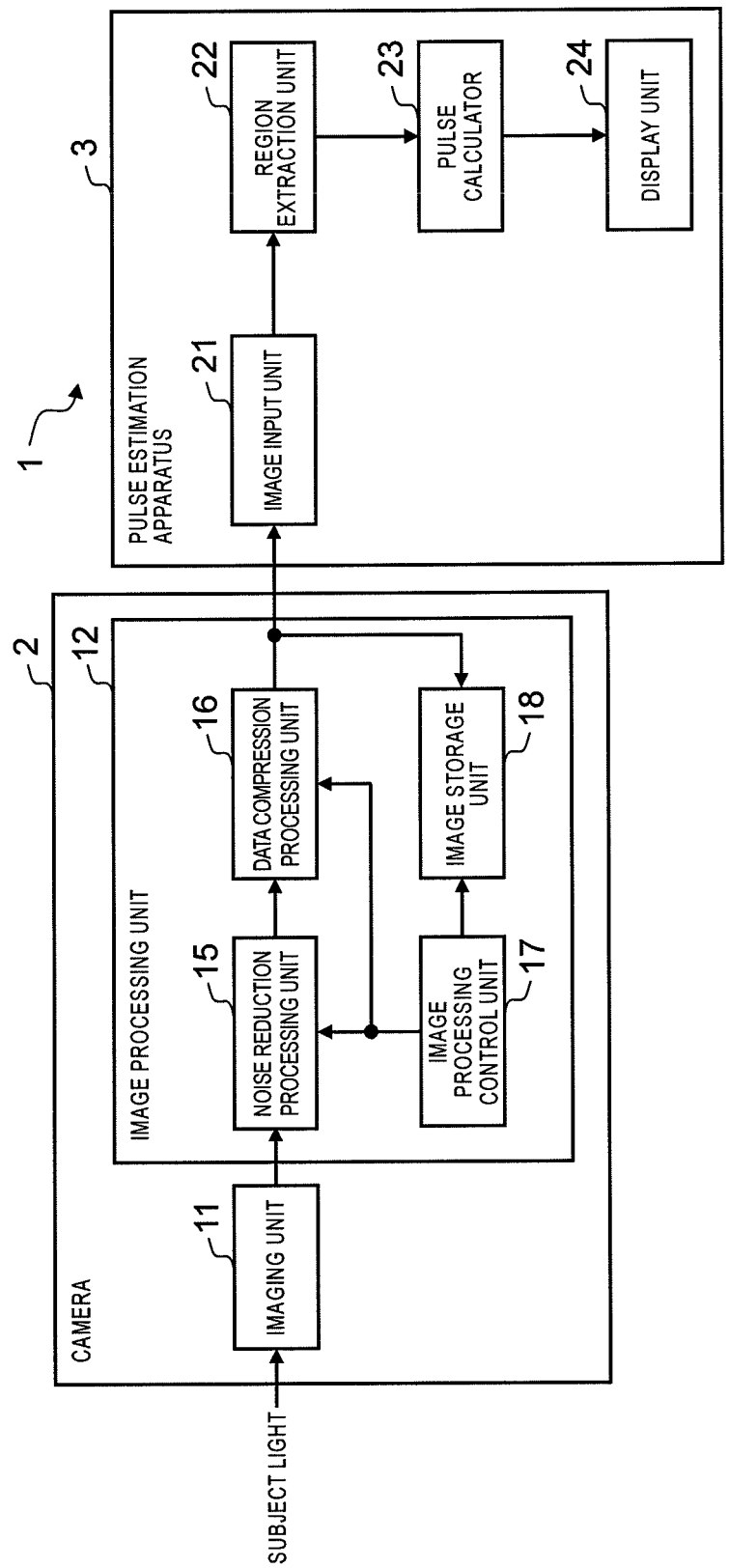
FIG. 2 is a block diagram of a function of the pulse estimation system.
Figure 3:
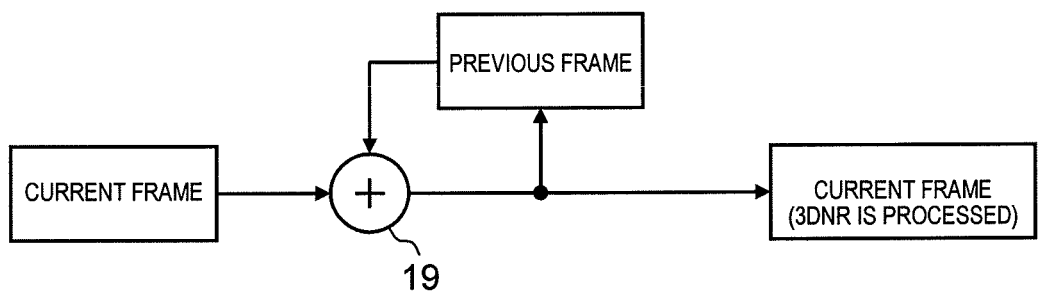
FIG. 3 is an explanatory view schematically illustrating processing by a noise reduction processing unit of a camera.
Figure 4:
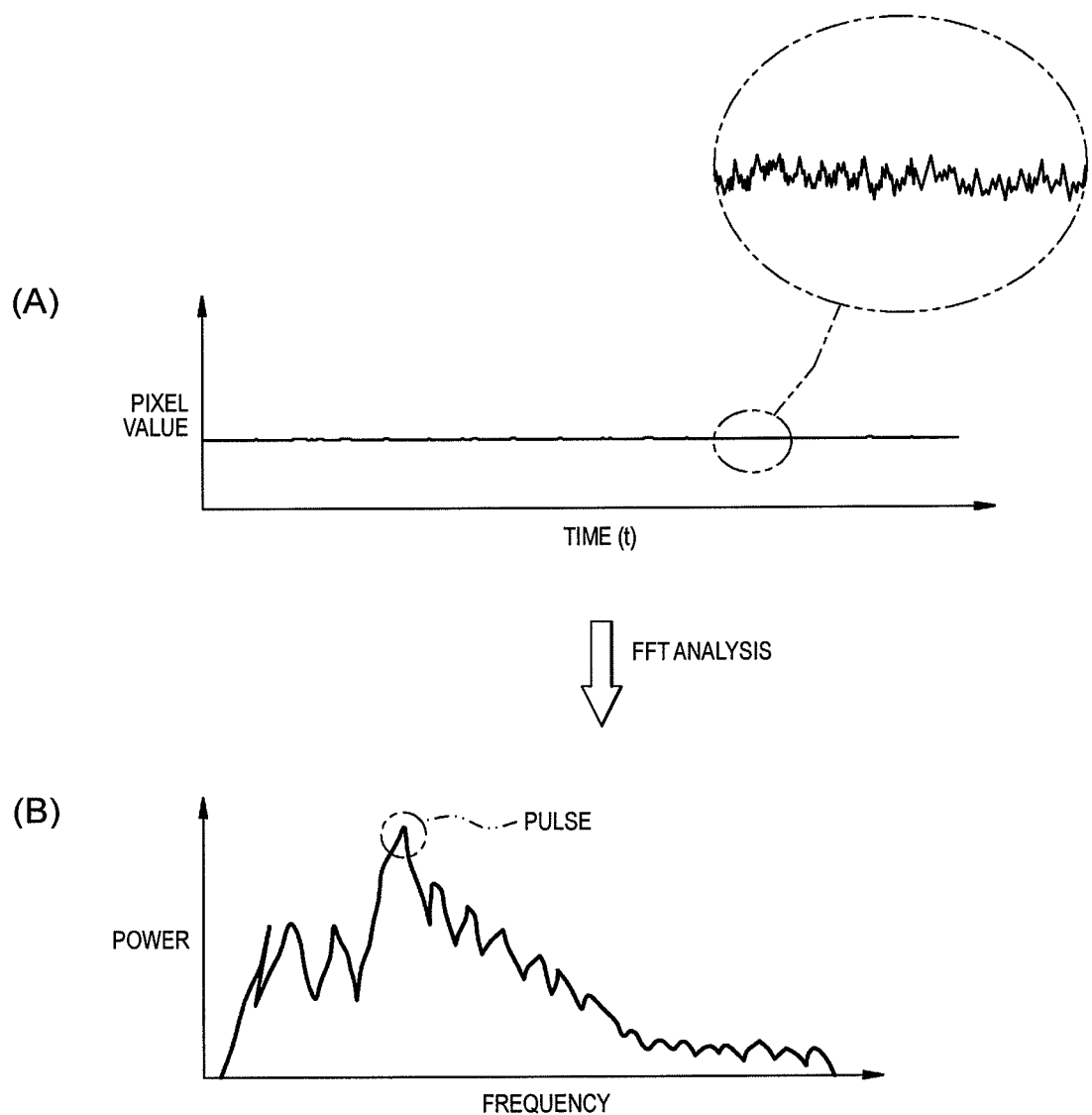
FIG. 4 is an explanatory view of pulse extraction processing by a pulse calculator of a pulse estimation apparatus.
Figure 5A:
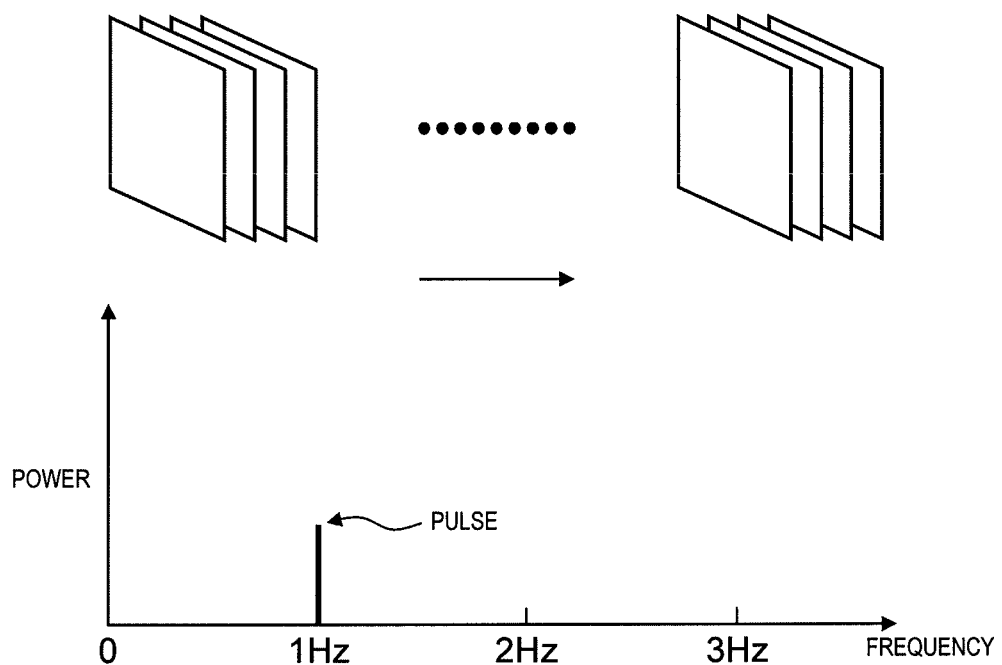
FIG. 5A is an explanatory view illustrating an example of noise that can occur in a data compression processing unit of the camera of a normal imaging mode.
Figure 5B:
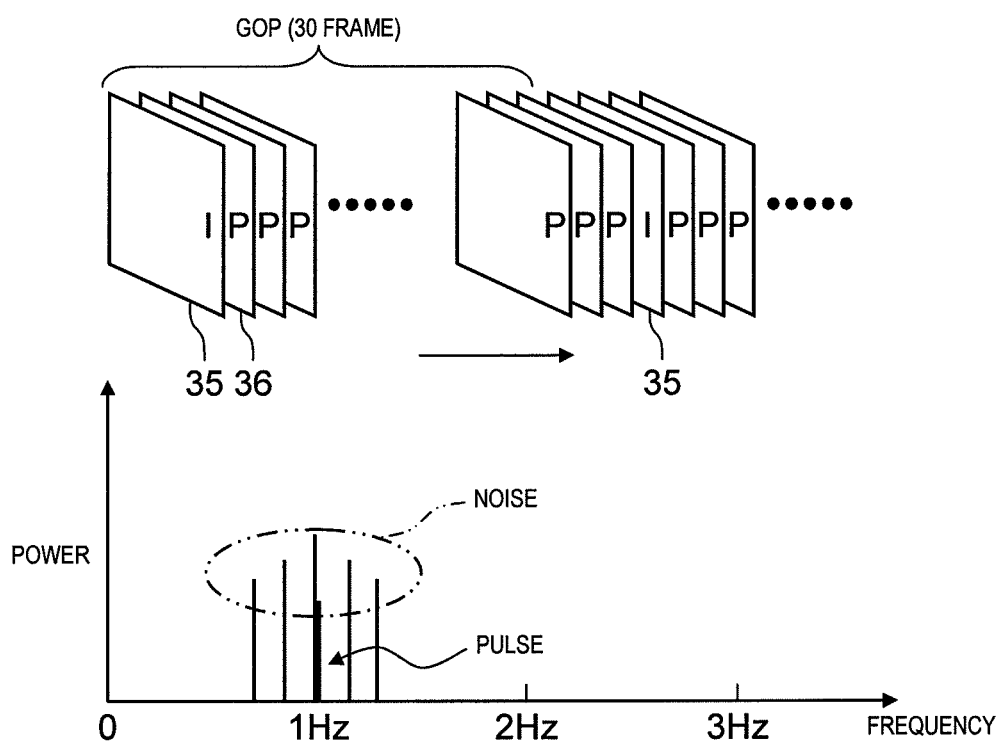
FIG. 5B is an explanatory view illustrating an example of noise that can occur in a data compression processing unit of the camera of a normal imaging mode.

FIGS. 1 and 2 are respectively a view of an entire configuration and a function block diagram of pulse estimation system 1 according to the present disclosure, FIG. 3 is an explanatory view schematically illustrating processing by noise reduction processing unit 15 of camera 2, FIG. 4 is an explanatory view of pulse extraction processing by pulse calculator 23 of pulse estimation apparatus 3, and FIGS. 5A and 5B are explanatory views illustrating an example of noise that can occur in data compression processing unit 16 of camera 2 of a normal imaging mode.

Pulse estimation system 1 is provided for estimating a pulse (usually equivalent to a heartbeat) from information (captured image) obtained without being in contact with a human body, and as illustrated in FIG. 1, includes camera (image processing apparatus) 2 that captures at least a part of person H that is a subject and pulse estimation apparatus 3 that estimates a pulse (pulse rate or pulse wave) of person H from a captured image (moving image) obtained by imaging of camera 2. In pulse estimation system 1, camera 2 and pulse estimation apparatus 3 are communicably connected to each other via network 4 such as an Internet or a Local Area Network (LAN). However, the configuration is not limited to this and camera 2 and pulse estimation apparatus 3 may be directly connected so as to be communicably by a known communication cable.

As illustrated in FIG. 2, camera 2 is a video camera having a known imaging function and as illustrated in FIG. 2, includes imaging unit 11 that images light from the subject on an image sensor (CCD, CMOS, or the like) through a lens mechanism (not illustrated), and image processing unit 12 that performs predetermined image processing on a captured image (digital video signal) input from imaging unit 11. Image processing unit 12 includes noise reduction processing unit 15 that executes noise reduction (noise reduction processing) for reducing or suppressing noise that degrades the image quality of a captured image, data compression processing unit 16 that executes processing (data compression processing) for compressing data of the captured image, image processing control unit (operation-mode selection unit) 17 that integrally controls an operation of each unit regarding various types of image processing including processing of noise reduction processing unit 15 and data compression processing unit 16, image storage unit 18 that stores the data of the captured image that is image-processed (here, noise reduction and data compression).

As described below, camera 2 includes a normal imaging mode (first operation mode) that executes image processing for normal imaging (for example, for person imaging, landscape imaging, or the like) and a vital information acquisition mode (second operation mode) that executes image processing for pulse estimation as the operation modes. Image processing control unit 17 can select one of the normal imaging mode and the vital information acquisition mode based on a command (for example, a button operation, a touch panel input, or the like) from a user. Image processing unit 12 is not limited to one illustrated in here, but it is possible to appropriately execute other known signal processing (for example, color tone correction, contour emphasis, or the like). Image processing unit 12 may be configured to further include other operation modes in addition to the normal imaging mode and the vital information acquisition mode described above.

Noise reduction processing unit 15 can execute three-dimensional noise reduction (3DNR) that reduces noise of the captured image based on a correlation between a plurality of temporarily adjacent frames as the noise reduction. More specifically, in noise reduction processing unit 15, as illustrated in FIG. 3, an image of a previous frame is added to an image of a current frame (pixel value) at a predetermined ratio in adder 19 (the current frame and the previous frame are synthesized based on a predetermined filter coefficient (M:N)), and thereby a 3DNR-processed current frame with improved S/N ratio is generated. For example, regarding the filter coefficient, image processing control unit 17 can set M:N=0.5:0.5 in the normal imaging mode and set M:N=0.9:0.1 in the vital information acquisition mode. The captured image subjected to the noise reduction is input into data compression processing unit 16.

Setting (or changing) of the filter coefficient is not limited to a method of setting one fitter coefficient for an entire image, but a method of setting for each divided region provided in an image may be adopted. For example, in the vital information acquisition mode, a skin color region (or a face region) is extracted from an image, the filter coefficient regarding a region other than the skin color region can be set to the same mode as the normal imaging mode, and the filter coefficient regarding the skin color region can be set to a different value from that of the normal imaging mode.

As described above, in the vital information acquisition mode, regarding information useful for the pulse estimation included in the captured image, information amount that is removed together with the noise from the captured image is suppressed by daringly reducing (reducing noise removing effect) the noise reduction.

Alternatively, in the vital information acquisition mode, the noise reduction may not be executed (the noise reduction is executed only in the normal imaging mode). Therefore, the information useful for the pulse estimation included in the captured image can be prevented from being removed together with the noise from the captured image in the vital information acquisition mode while appropriately reducing the noise of the captured image in the normal imaging mode.

Noise reduction processing unit 15 includes an extraction function of the face region in the same captured image as that of region extraction unit 22 which is described below and thereby in a case where the face region is extracted from the captured image, as described above, the noise reduction processing may be reduced only in the face region, or the noise reduction processing may not be executed only in the face region. Therefore, the same effect as that described above can be obtained while appropriately reducing the noise other than the face region.

Data compression processing unit 16 can execute the data compression processing of the captured image based on the MPEG standard data encoding method. The captured image (compressed image) which is data compression-processed is stored in image storage unit 18 and is transmitted to pulse estimation apparatus 3 if necessary (in a case where the vital information acquisition mode is executed).

Although not illustrated, camera 2 described above, for example, includes a processor that collectively executes various types of image processing, control of peripheral devices, or the like based on a predetermined capturing control program, a Random Access Memory (RAM) as a volatile memory that functions as a wok area of the processor, a Read Only Memory (ROM) as a nonvolatile memory that stores a control program executed by the processor and data, an auxiliary storage device, and the like. The function of each unit of image processing unit 12 as described above is executed by hardware and the capturing control program executed by the processor.

In pulse estimation system 1, at least one of the noise reduction and the data compression processing may be executed, and thereby at least one of noise reduction processing unit 15 and data compression processing unit 16 may be omitted in image processing unit 12. At least a part of functions (the noise reduction, the data compression processing, and the like) of image processing unit 12 in camera 2 may be executed by another apparatus (for example, pulse estimation apparatus 3) of pulse estimation system 1.

Pulse estimation apparatus 3 includes image input unit 21 into which the captured image (video signal) from camera 2 is input as a temporarily continuous captured image including at least a part of person H, region extraction unit 22 that extracts the skin color region (here, the face region) of person H from the captured image, pulse calculator (pulse estimation unit) 23 that calculates (estimates) the pulse of person H based on the extracted skin color region of person H, and display unit 24 that includes a known display device capable of displaying various kinds of information including an estimation result of the pulse to the user. The skin color region extracted by region extraction unit 22 is a region in which the skin is exposed in the human body and is a region in which the pulse can be estimated from captured image data of the region. The captured image input into image input unit 21 is not limited to being transmitted from camera 2, and may be a captured image stored in a known memory or the like after the image is captured.

Region extraction unit 22 executes known face detection processing for recognizing a feature amount of the face with respect to each captured image (frame image), thereby extracting and tracking the detected region of the face as the skin color region of person H. Region extraction unit 22 transmits data of the captured image regarding the extracted face region to pulse calculator 23.

In region extraction unit 22, it is not limited to the method described above, but pixels, which have a skin color component (for example, a preset ratio with respect to each pixel value of RGB, which is a value different depending on race or the like) that is preset from the captured image, are extracted and a region in which the pixels are extracted may be the skin color region. In this case, a portion (for example, hand, arm, or the like) in which the skin other than the face is exposed can be extracted as the skin color region. However, as described above, there is an advantage that it is possible to easily extract the skin color region by extracting the face region of person H as the skin color region. Only one person H is illustrated in FIG. 1, but in a case where a plurality of persons are included in the captured image, a plurality of face regions can be extracted in region extraction unit 22.

Pulse calculator 23 calculates, for example, pixel values (0-255 gradations) of each component of the RGB regarding each pixel configuring the skin color region extracted in the temporarily continuous captured image, and generates time series data of a representative value (here, an average value of respective pixels) as a pulse signal. Here, the average value of respective pixels is used as the representative value and the average value is a value of decimal point precision. In this case, it is possible to generate the time series data based on a pixel value of only a green component (G) of which variation is particularly large due to pulsation.

For example, as illustrated in (A) of FIG. 4, the time series data of the generated pixel value (average value) can be detected as a minute variation (for example, variation less than one gradation of the pixel value) based on a change in hemoglobin concentration in the blood. Therefore, pulse calculator 23 executes frequency analysis processing by a Fast Fourier Transform (FFT) on the time series data based on the pixel value, thereby being capable of extracting a power spectrum as illustrated in (B) of FIG. 4. In pulse calculator 23, a frequency component (for example, a maximum value of a spectrum) having high power can be detected in the power spectrum and the pulse (pulse rate) can be estimated based on the frequency component.

Pulse estimation apparatus 3 described above can be configured of, for example, an information processing apparatus such as a personal computer (PC). Although not illustrated, pulse estimation apparatus 3 has a hardware configuration including a processor that collectively executes various types of information processing, control of peripheral devices, or the like based on a predetermined control program, a RAM as a volatile memory that functions as a wok area of the processor, a ROM as a nonvolatile memory that stores a control program executed by the processor and data, a network interface that executes communication processing via a network, a monitor (image output device), a speaker, an input device, a Hard Disk Drive (HDD), and the like. At least a part of the function of each unit of pulse estimation apparatus 3 illustrated in FIG. 2 can be realized by executing a predetermined control program. At least a part of the function of pulse estimation apparatus 3 may be replaced by other known hardware processing.

Here, noise that can occur in the data compression processing in data compression processing unit 16 will be described with reference to FIGS. 5A and 5B. FIG. 5A illustrates a frequency analysis result in a case where the data compression processing is not executed in the captured image for comparison. In FIG. 5A, for the sake of convenience of explanation, only a spectrum based on the pulse is schematically illustrated. On the other hand, FIG. 5B illustrates a frequency analysis result in a case where I picture 35 is periodically inserted at intervals of 30 frames at a head of a Group of Picture (GOP) configured of I picture 35 and P pictures 36 with respect to a captured image at a frame rate of 30 fps. In FIG. 5B, for the sake of convenience of explanation, only the spectrum based on the pulse and noise based on the data compression processing are schematically illustrated.

As illustrated in FIG. 5A, in a case where the data compression processing is not executed, for example, when the pulse rate is approximately 60 beats/minutes, a spectrum appears at a position of a frequency of approximately 1 Hz based on the pulse, and the pulse can be estimated based on the spectrum.

On the other hand, as illustrated in FIG. 5B, in a case where I picture 35 is inserted at the intervals of 30 frames in the captured image of the frame rate of 30 fps, the noise occurs in a frequency range close to the frequency (approximately 1 Hz) of the pulse by switching from I picture 35 to subsequent P picture 36. This is considered that a difference between information amounts lost at the time of switching between I picture 35 and P picture 36 appears as the spectrum in the frequency analysis. Therefore, it becomes difficult to distinguish between the spectrum and the noise based on the pulse, and as a result, it is difficult to estimate the pulse based on the spectrum as illustrated in (B) of FIG. 4.

Therefore, in pulse estimation system 1, as described below, image processing control unit 17 changes (controls the GOP) a temporal interval of the I picture inserted into the GOP configured of a plurality of pictures (I picture, P picture, and B picture) depending on an operation mode of camera 2, thereby being capable of acquiring the captured image suitable for the estimation of the pulse.

In the embodiment, the frame rate of the captured image is 30 fps, but the face region is not limited to the embodiment, and even at other frame rates, noise caused by the insertion of the I picture in a vicinity of the spectrum based on the pulse may occur depending on the insertion interval of the I picture in the GOP. Here, although attention is paid to the noise occurred by switching from the I picture to the P picture, this also applies to noise occurred by switching from the I picture to the B picture.

Figure 6:
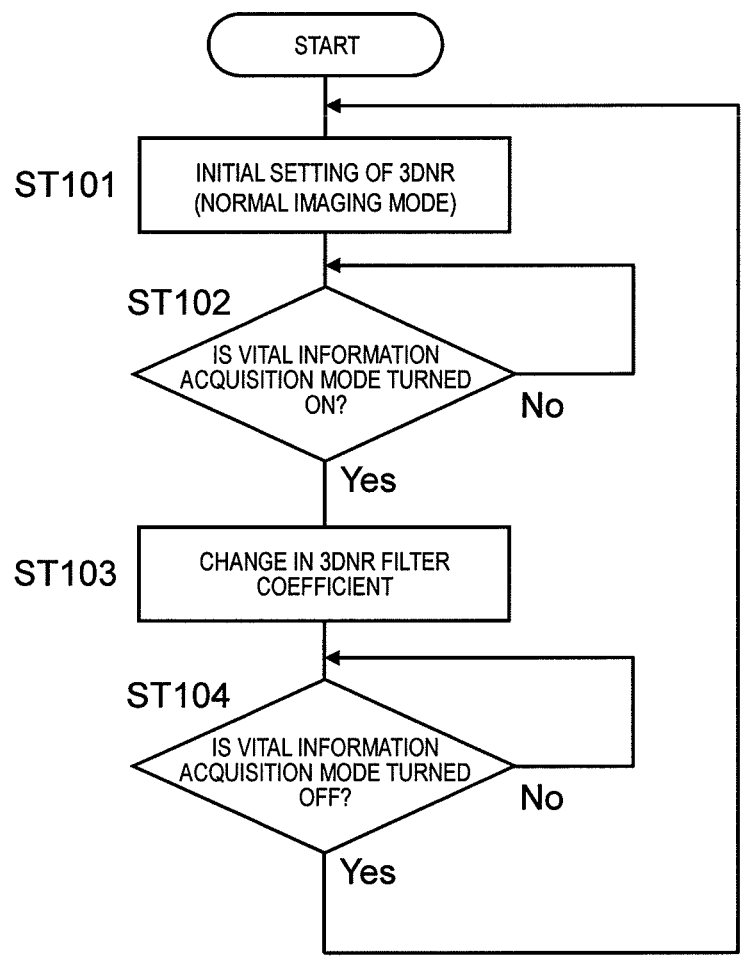
FIG. 6 is a flowchart illustrating a setting method regarding noise reduction in a noise reduction processing unit of a camera.

FIG. 6 is a flowchart illustrating a setting method regarding noise reduction in noise reduction processing unit 15 of camera 2. When camera 2 is activated, image processing control unit 17 executes initial setting regarding the noise reduction of noise reduction processing unit 15 (ST101). In the embodiment, when camera 2 is activated, the normal imaging mode is selected (ON), and image processing control unit 17 sets a filter coefficient of 3DNR to an initial value (here, M:N=0.5:0.5) regarding the noise reduction. Therefore, the user can acquires the captured image in which the noise is appropriately reduced in the normal imaging by camera 2.

Subsequently, if the vital information acquisition mode is selected (ON) based on a command of the user (ST102: Yes), image processing control unit 17 changes the filter coefficient of 3DNR (here, changes to M:N=0.9:0.1) so that the ratio of the image of the previous frame which is synthesized to the image of the current frame is reduced (ST103). In this case, the captured image subjected to slight noise reduction that does not hinder the pulse estimation processing in pulse estimation apparatus 3 is output from camera 2 to pulse estimation apparatus 3. Therefore, the captured image suitable for the pulse estimation processing can be acquired while reducing the noise of the captured image to some extent (that is, while maintaining the image quality of the captured image as much as possible).

Alternatively, in step ST103, image processing control unit 17 may turn off three-dimensional noise reduction (sets to M:N=1.0:0.0). In this case, the captured image that is not subjected to the noise reduction is output from camera 2 to pulse estimation apparatus 3. Therefore, although a noise reduction effect is not obtained, it is possible to acquire the captured image further suitable for the pulse estimation processing.

When the vital information acquisition mode is finally turned off (here, the normal imaging mode is selected) (ST104: Yes), the process returns to step ST101 again and the same steps as those described above are repeatedly executed. As the setting method of the noise reduction, the vital information acquisition mode may be selected (ON) when camera 2 is activated (started from step ST103).

Figure 7:
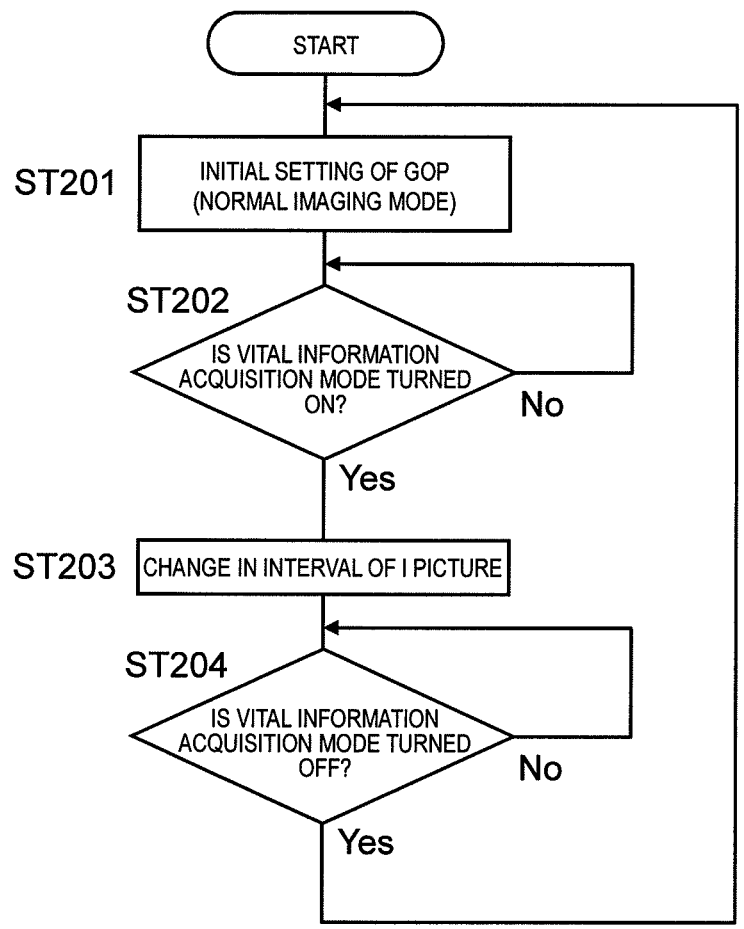
FIG. 7 is a flowchart illustrating a setting method regarding data compression processing in a data compression processing unit of a camera.
Figure 8:
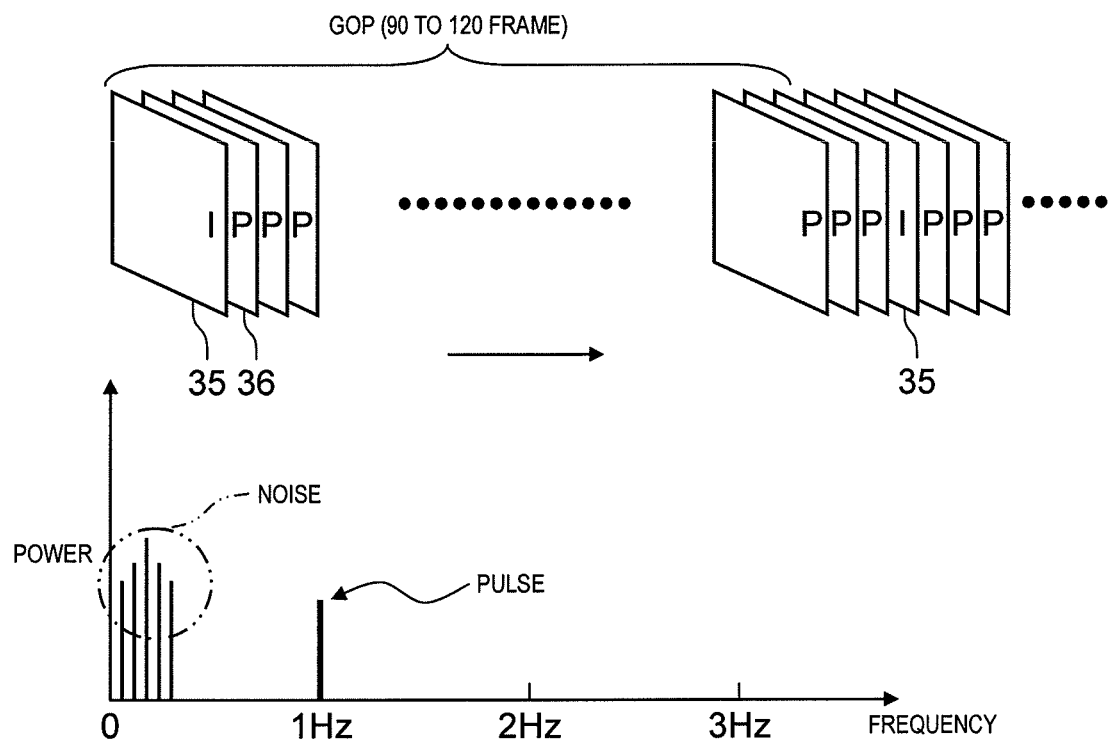
FIG. 8 is an explanatory view illustrating processing of step ST203 of FIG. 7 and a processing result thereof.
Figure 9:
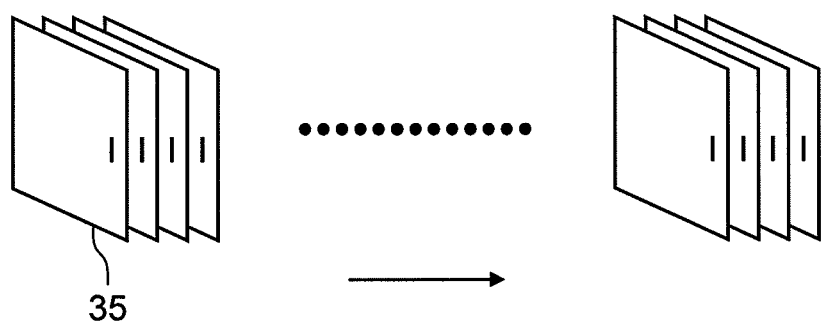
FIG. 9 is an explanatory view illustrating a modification example of processing of FIG. 8 and a processing result.

FIG. 7 is a flowchart illustrating a setting method regarding data compression processing in data compression processing unit 16 of camera 2, FIG. 8 is an explanatory view illustrating processing of step ST203 of FIG. 7 and a processing result thereof, and FIG. 9 is an explanatory view illustrating a modification example of processing illustrated in FIG. 8 and a processing result.

When camera 2 is activated, image processing control unit 17 executes an initial setting regarding the data compression processing of data compression processing unit 16 (ST201). In the embodiment, when camera 2 is activated, the normal imaging mode is selected (ON), and image processing control unit 17 sets the I picture in the captured image (compressed image) of the frame rate of 30 fps regarding the data compression processing so as to inserting the I picture at intervals of 30 frames. Therefore, the user can acquire the captured image of which a data capacity is appropriately compressed in the normal imaging.

Subsequently, if the vital information acquisition mode is selected (ON) based on a command of the user (ST202: Yes), image processing control unit 17 changes the insertion interval of the I picture regarding the data compression processing (ST203). In this case, as illustrated in FIG. 8, image processing control unit 17 sets I picture 35 so that I picture 35 is inserted between a group of P pictures 36, for example, at frame intervals of appropriately 90 to 120. Therefore, since the noise (see FIG. 5B) occurring in a frequency range close to the frequency of the pulse is displaced to a lower frequency side than the frequency component (here, appropriately 1 Hz) of the pulse, in the pulse estimation processing in pulse estimation apparatus 3, the spectrum and the noise are easily distinguished based on the pulse.

Alternatively, for example, as illustrated in FIG. 9, image processing control unit 17 may set an entire frame so that the entire frame is configured of I pictures 35 instead of changing the insertion interval of the I picture in step ST203. In this case, although the effect of the data compression is reduced, the generation of the noise caused by switching from the I picture to the P picture can be reliably prevented.

When the vital information acquisition mode is finally turned off (here, the normal imaging mode is selected) (ST204: Yes), the process returns to step ST201 again and the same steps as those described above are repeatedly executed. As the setting method of the data compression processing, the vital information acquisition mode may be selected (ON) when camera 2 is activated (started from step ST203).

OUTLINE OF THE PRESENT DISCLOSURE

The image processing apparatus of the present disclosure acquires an image for estimating the pulse. The image processing apparatus includes a data compression processing unit that executes data compression processing on an input captured image based on inter-frame prediction; and an operation-mode selection unit that is capable of selecting one of a first operation mode for normal imaging and a second operation mode for pulse estimation based on a command from a user. In a case where the second operation mode is selected, the data compression processing unit sets an interval between I pictures constituting a compressed image generated by the data compression processing to an interval to be different from that in a case where the first operation mode is selected.

According to the image processing apparatus of the present disclosure, in the first operation mode for the normal imaging, even in a case where the noise having the frequency close to the frequency component of the pulse occurs caused by the interval of the I picture (that is, switching from the I picture to another picture), in the second operation mode for the pulse estimation, the data compression processing of the image is appropriately executed (that is, the interval of the I picture is set to a different interval from that of a case where the first operation mode is selected). Therefore, it is possible to acquire the image suitable for the estimation of the pulse while suppressing an increase in the data amount of the image.

In the image processing apparatus of the present disclosure, in a case where the second operation mode is selected, the data compression processing unit may set the interval between the I pictures to a greater interval than that of a case where the first operation mode is selected.

According to the image processing apparatus of the present disclosure, in the second operation mode for the pulse estimation, the interval of the I picture is set a greater interval than that of a case where the first operation mode is selected. Therefore, the noise occurring caused by the interval of the I picture can be displaced to a lower frequency side than the frequency component of the pulse. As a result, it is possible to acquire an image suitable for the estimation of the pulse.

In the image processing apparatus of the present disclosure, in a case where the first operation mode is selected, the data compression processing unit may form the compressed image with at least the I picture and the P picture, and in a case where the second operation mode is selected, may form the compressed image only with the I picture.

According to the image processing apparatus of the present disclosure, in the second operation mode for the pulse estimation, it is possible to reliably prevent occurrence of the noise caused by the interval (switching to the P picture or the like) of the I picture by forming the compressed image only by the I picture. As a result, it is possible to acquire an image suitable for the estimation of the pulse.

In the image processing apparatus of the present disclosure, the image processing apparatus may further include a noise reduction processing unit that executes noise reduction processing of the captured image.

In a case where the second operation mode is selected, the noise reduction processing unit may reduce the noise reduction processing more than that of a case where the first operation mode is selected.

According to the image processing apparatus of the present disclosure, in the second operation mode for the pulse estimation, it is possible to suppress the information amount removed together with the noise from the captured image regarding information useful for the pulse estimation included in the captured image by reducing the noise reduction processing. As a result, it is possible to acquire an image suitable for the estimation of the pulse.

In the image processing apparatus of the present disclosure, the image processing apparatus may further include a noise reduction processing unit that executes noise reduction processing of the captured image. In a case where the first operation mode is selected, the noise reduction processing unit may execute the noise reduction processing, and on the other hand, in a case where the second operation mode is selected, may not execute the noise reduction processing.

According to the image processing apparatus of the present disclosure, in the second operation mode for the pulse estimation, the noise reduction processing is not executed. Therefore, information useful for the pulse estimation included in the captured image can be prevented from being removed together with the noise from the captured image. As a result, it is possible to acquire an image suitable for the estimation of the pulse.

In the image processing apparatus of the present disclosure, in a case where a face region is extracted from the captured image, the noise reduction processing unit may reduce the noise reduction processing only in the face region, or may not execute the noise reduction processing only in the face region.

According to the image processing apparatus of the present disclosure, in the second operation mode for the pulse estimation, the noise reduction processing is reduced only in the face region, or the noise reduction processing is not executed only in the face region. Therefore, information for the pulse estimation included in the captured image can be suppressed or prevented from being removed together with the noise from the captured image while appropriately reducing the noise other than the face region.

A pulse estimation system of the present disclosure may include the image processing apparatus, and a pulse estimation apparatus that estimates a pulse based on a compressed image executed by the data compression processing in the image processing apparatus.

According to the pulse estimation system of the present disclosure, in the first operation mode for the normal imaging in the image processing apparatus, even in a case where the noise having the frequency close to the frequency component of the pulse caused by the interval of the I picture occurs, in the second operation mode for the pulse estimation, the data compression processing of the image is appropriately executed. Therefore, it is possible to acquire an image suitable for the estimation of the pulse in the pulse estimation apparatus while suppressing an increase in the data amount of the image.

An image processing method of the present disclosure acquires an image for estimating the pulse. The image processing method includes a data compression processing step of executing data compression processing on an input captured image based on inter-frame prediction, and an operation-mode selecting step of selecting one of a first operation mode for normal imaging and a second operation mode for pulse estimation based on a command from a user. In the data compression processing step, in a case where the second operation mode is selected, an interval between I pictures constituting a compressed image generated by the data compression processing is set to an interval to be different from that in a case where the first operation mode is selected.

According to the image processing method of the present disclosure, in the first operation mode for the normal imaging, even in a case where the noise having the frequency close to the frequency component of the pulse caused by the interval of the I picture occurs, in the second operation mode for the pulse estimation, the data compression processing of the image is appropriately executed. Therefore, it is possible to acquire an image suitable for the estimation of the pulse while suppressing an increase in the data amount of the image.

Although the present disclosure is described based on specific embodiments, these embodiments are merely examples, and the present disclosure is not limited by these embodiments. For example, in the embodiments, an example in which the image processing apparatus according to the present disclosure is realized as a part of the function of camera 2 is illustrated, but the image processing apparatus is not limited to the example, but may be an apparatus that executes the data compression processing (or the noise reduction) of the captured image acquired from camera 2. In addition, the captured image which is image-processed by camera 2 is not necessarily and directly transmitted to pulse estimation apparatus 3, but the captured image stored in image storage unit 18 may be separately used for the estimation of the pulse by another apparatus. All of the image processing apparatus, the pulse estimation system having the same, and the image processing method are not necessarily essential, and can be appropriately selected at least as long as they do not depart from the scope of the present disclosure.

INDUSTRIAL APPLICABILITY

The image processing apparatus, the pulse estimation system having the same, and the image processing method according to the present disclosure can acquire an image suitable for the estimation of the pulse while suppressing an increase of the data amount of the image by appropriately executing the data compression processing of the image, and are useful as an image processing apparatus, a pulse estimation system having the same, and an image processing method for acquiring an image suitable for the estimation of the pulse.

REFERENCE MARKS IN THE DRAWINGS

1 PULSE ESTIMATION SYSTEM
2 CAMERA (IMAGE PROCESSING APPARATUS)
3 PULSE ESTIMATION APPARATUS
11 IMAGING UNIT
12 IMAGE PROCESSING UNIT
15 NOISE REDUCTION PROCESSING UNIT
16 DATA COMPRESSION PROCESSING UNIT
17 IMAGE PROCESSING CONTROL UNIT (OPERATION-MODE SELECTION UNIT)
18 STORAGE UNIT
21 IMAGE INPUT UNIT
22 REGION EXTRACTION UNIT
23 PULSE CALCULATOR

The invention claimed is:

1. An image processing apparatus that acquires an image for estimating a pulse, comprising:
a processor that:
executes data compression processing on an input captured image based on inter-frame prediction; and
selects one of a first operation mode for normal imaging and a second operation mode for pulse estimation based on a command of a user,
wherein in a case where the first operation mode is selected, the processor sets an interval between I pictures to be of a first value such that a frequency component of a pulse overlaps with a frequency component of noise of the data compression processing,
wherein in a case where the second operation mode is selected, the processor modifies the interval between I pictures to be of a second value different from the first value to perform the pulse estimation, such that the frequency component of the pulse does not overlap with the frequency component of the noise of the data compression processing,
wherein the pulse estimation is performed during the second operation mode and not in the first operation mode, and
wherein each of the I pictures constitute a compressed image generated by the data compression processing.

2. The image processing apparatus of claim 1,
wherein in a case where the second operation mode is selected, the processor sets the interval between the I pictures to a greater interval than that of a case where the first operation mode is selected.

3. The image processing apparatus of claim 1,
wherein in a case where the first operation mode is selected, the processor constitutes the compressed image with at least the I picture and a P picture, and in a case where the second operation mode is selected, the processor constitutes the compressed image only with the I picture.

4. The image processing apparatus of claim 1,
wherein the processor executes noise reduction processing of the captured image, and
wherein in a case where the second operation mode is selected, the processor reduces the noise reduction processing more than that of a case where the first operation mode is selected.

5. The image processing apparatus of claim 1,
wherein the processor executes noise reduction processing of the captured image, and
wherein in a case where the first operation mode is selected, the processor executes the noise reduction processing, and in a case where the second operation mode is selected, the processor does not execute the noise reduction processing.

6. The image processing apparatus of claim 4,
wherein in a case where a face region is extracted from the captured image, the processor reduces the noise reduction processing only in the face region, or does not execute the noise reduction processing only in the face region.

7. A pulse estimation system comprising:
the image processing apparatus of claim 1; and
a pulse estimation apparatus that estimates a pulse based on a compressed image executed by the data compression processing in the image processing apparatus.

8. An image processing method for acquiring an image for estimating a pulse, the method comprising:
executing data compression processing on an input captured image based on inter-frame prediction; and
selecting one of a first operation mode for normal imaging and a second operation mode for pulse estimation based on a command from a user,
wherein in a case where the first operation mode is selected, setting an interval between I pictures to be of a first value such that a frequency component of a pulse overlaps with a frequency component of noise of the data compression processing,
wherein in a case where the second operation mode is selected, an interval between I pictures is modified to a second value different from the first value to perform pulse estimation, such that the frequency component of the pulse does not overlap with the frequency component of the noise of the data compression processing,
wherein the pulse estimation is performed during the second operation mode and not in the first operation mode, and
wherein each of the I pictures constitute a compressed image generated by the data compression processing.

* * * * *